United States Patent
Sarac (10) Patent No.: US 7,559,953 B2
(45) Date of Patent: Jul. 14, 2009

(54) METHOD FOR FIXING TISSUE (75) Inventor: Timur Paul Sarac, Orange Village, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 765 days.

(21) Appl. No.: 11/029,687

(22) Filed: Jan. 5, 2005

(65) Prior Publication Data
US 2005/0119728 A1   Jun. 2, 2005

Related U.S. Application Data (60) Continuation-in-part of application No. 10/409,884, filed on Apr. 9, 2003, now Pat. No. 7,137,947, which is a division of application No. 09/908,764, filed on Jul. 19, 2001, now Pat. No. 6,579,307.

(51) Int. Cl.
A61F 2/02   (2006.01)

(52) U.S. Cl. ............... 623/23.72; 623/23.76; 623/1.24; 623/915; 600/36

(58) Field of Classification Search .................. None
See application file for complete search history.

(56) References Cited

U.S. PATENT DOCUMENTS

| | | | |
|---|---|---|---|
| 4,969,896 A | 11/1990 | Shors | |
| 5,192,311 A | 3/1993 | King et al. | |
| 5,429,144 A | 7/1995 | Wilk | |
| 5,480,424 A | 1/1996 | Cox | |
| 5,556,414 A | 9/1996 | Turi | |
| 5,562,727 A | 10/1996 | Turk et al. | |
| 5,667,523 A | 9/1997 | Bynon et al. | |
| 5,693,085 A | 12/1997 | Buirge et al. | |
| 5,865,723 A | 2/1999 | Love | |
| 5,876,432 A | 3/1999 | Lau et al. | |
| 5,891,193 A | 4/1999 | Robinson et al. | |
| 6,077,217 A | 6/2000 | Love et al. | |
| 6,245,100 B1 | 6/2001 | Davila et al. | |
| 6,331,191 B1 | 12/2001 | Chobotov | |
| 6,355,055 B1 | 3/2002 | Waksman et al. | |
| 6,358,275 B1 | 3/2002 | McIlroy et al. | |
| 6,468,300 B1 | 10/2002 | Freidberg | |
| 6,475,232 B1 | 11/2002 | Babbs et al. | |
| 6,579,307 B2 | 6/2003 | Sarac | |
| 2001/0041928 A1 | 11/2001 | Pavcnik et al. | |
| 2002/0123789 A1* | 9/2002 | Francis et al. | 623/1.13 |
| 2002/0146393 A1 | 10/2002 | Bell et al. | |
| 2003/0014126 A1* | 1/2003 | Patel et al. | 623/23.72 |
| 2004/0030405 A1 | 2/2004 | Carpentier et al. | |
| 2004/0236411 A1 | 11/2004 | Sarac et al. | |

FOREIGN PATENT DOCUMENTS

WO   WO 97/09006 A1   3/1997

OTHER PUBLICATIONS

Sarac et al. "In vivo and mechanical properties of peritoneum/fascia as a novel arterial substitute." Journal of Vascular Surgery, 2004; 41:490-497.

* cited by examiner

Primary Examiner—David H Willse
Assistant Examiner—Javier G Blanco
(74) Attorney, Agent, or Firm—Tarolli, Sundheim, Covell & Tummino LLP (57) ABSTRACT A method of preparing a fixed biological tissue includes, shaping the biological tissue, cross-linking the biological tissue, sterilizing the biological tissue, and inactivating prions in the biological tissue.

14 Claims, 9 Drawing Sheets

METHOD FOR FIXING TISSUE

RELATED APPLICATIONS

This application is a continuation-in-part of U.S. patent application Ser. No. 10/409,884, now U.S. Pat. No. 7,137,947, filed Apr. 9, 2003 which is a divisional of U.S. patent application Ser. No. 09/908,764, filed Jul. 19, 2001 (now U.S. Pat. No. 6,579,307).

TECHNICAL FIELD

The present invention relates, in general, to tissue fixation and, in particular, to methods of treating tissues so as to prepare them for implantation/transplantation.

BACKGROUND OF THE INVENTION

Surgical procedures in which a cardiovascular prosthesis is implanted into a patient's blood vessel are common in treating many vascular disorders. For example, one common type of cardiovascular prosthesis is an endovascular prosthesis that is used to strengthen a blood vessel wall in the location of an aneurysm, or to open an occlusion in a blood vessel.

A typical endovascular prosthesis includes a flexible, tubular member, made of fabric or polytetrafluoroethylene (PTFE), that may be anchored with sutures or carried by one or more support structures known as stents. Generally, each stent is formed from a material having an elasticity sufficient to permit radial expansion of the stent and having a strength sufficient to prevent radial collapse or burst. Such stents are typically formed from stainless steel, titanium, Nitinol, or a suitable plastic.

A common endeavor in the field of cardiovascular prosthetics is to increase the patency rate of prostheses. Thrombosis and platelet deposition on surfaces of a cardiovascular prosthesis reduce the patency rate of the prosthesis. For example, thrombosis and platelet deposition within an endovascular prosthesis may occlude the conduit defined by the endovascular prosthesis.

Many factors contribute to thrombosis and platelet deposition on the surfaces of known cardiovascular prosthesis. The most common factors are dependent upon the material or materials forming the inner surface of the conduit of the endovascular prosthesis. Typically, thrombosis and platelet deposition begin to occlude the conduit of the endovascular prosthesis when the material or materials forming the conduit of the endovascular prosthesis are foreign to the patient's body. A thrombus begins to form on the inner surface of the conduit of the endovascular prosthesis and extends annularly about the inner surface of the conduit. Eventually, the thrombus can severely restrict blood flow through the conduit defined by the endovascular prosthesis and, if left untreated, can completely occlude the conduit.

Additionally, thrombosis and platelet deposition may occur as a result of irregularities on the inner surface of a cardiovascular prosthesis. The irregularities may be formed by the structure of an inner stent that is used to support the cardiovascular prosthesis, or may be formed by the inner surface of the flexible member used for the prosthesis.

To reduce the occurrence of thrombosis and platelet deposition, the inner surface of endovascular prosthetics may be lined with biological tissue. Lining the inner surface of endovascular prostheses with biological tissue may help to reduce thrombosis and platelet deposition by providing an established protein scaffold upon which endogenous tissue cells can readily adhere and proliferate.

Biological material is typically stabilized prior to implantation. This process of stabilization, also known as fixation or tanning, usually consists of a series of chemical steps whereby: (1) the tissue's biomechanical properties are stabilized; (2) the tissue is sterilized; and (3) the antigenicity of the tissue is reduced.

SUMMARY OF THE INVENTION

The present invention relates to a method of preparing a fixed biological tissue. In the method, at least one layer of biological tissue is harvested. The biological tissue can be selected from the group consisting essentially of pericardial tissue, peritoneal tissue, and pleural tissue. The biological tissue is shaped by, for example, cutting the biological tissue and suturing the biological tissue to a member (e.g., polyethylene plate). The biological tissue is also at least partially cross-linked. The biological tissue can be cross-linked by contacting the biological tissue with an aldehyde. The biological tissue is further sterilized, by, for example, contacting the biological tissue with a solution containing an alcohol. Additionally, prions and other infectious or virus related products in the tissue are inactivated. The prions and other infectious or virus related products can be inactivated by, for example, contacting the biological tissue with a basic solution.

Optionally, in order to form an acellular fixed biological tissue, the biological tissue can be contacted with a solution that affects cell lysis. The cell lysis solution can comprise a hypertonic solution with a salt concentration greater than the salt concentration of the cells of the biological tissue.

Biological tissue fixed by this method can be used, for example, as a graft that can be positioned within a patient's vasculature. When utilized within a patient's vasculature, the fixed biological tissue is readily endothelized. Ready endothelization of the biological tissue mitigates the formation of clots within the vasculature and promotes biocompatibility of the biological tissue.

In another aspect of the invention, the method can comprise harvesting at least one layer of biological tissue, shaping the layer of harvested biological tissue, at least partially cross-linking the shaped biological tissue, sterilizing the at least partially cross-linked biological tissue, and inactivating prions in the sterilized biological tissue. The method can also comprise applying at least one pharmacological agent to the fixed biological tissue. The pharmacological agent comprises at least one of an anti-inflammatory agent, an anti-proliferative agent, an anti-coagulation agent, or an anti-platelet aggregation agent.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

The present invention relates to methods of fixing or preserving a layer of biological tissue and to a layer of biological tissue fixed or preserved by one of the methods. The layer of biological tissue fixed or preserved by one of the methods can be transplanted or implanted in a part of a body to repair a defect.

The biological tissue that is fixed by one of the methods in accordance with the present invention includes an inner lining and an outer lining. The inner lining is a serous membrane and the outer lining is fascia associated with the serous membrane. The biological tissue of the present invention may be derived from a range of animal species, such as human, bovine, equine, porcine, murine, avian, and combinations thereof. According to one aspect of the invention, the biological tissue is autogenous tissue. Alternatively, cadaveric tissue or xenogeneic tissue may be used.

According to one embodiment of the present invention, the layer of biological tissue is harvested from the peritoneum. Alternatively, the biological tissue may be harvested from the pericardium or from the pleura. As an alternative to a layer of natural biological tissue, an artificially constructed layer of biological tissue that mimics the characteristics of peritoneal, pleural, or pericardial membrane may be used. The artificially constructed biological tissue may be formed from collagen scaffolding that is seeded with tissue cells, such as human keratinocytes. The artificially constructed biological tissue may also include a basement membrane. The basement membrane may be a fascia lining or another known artificial lining.

The biological tissue in accordance with the invention can be harvested in sheets or layers of appropriate size based on the intended application of the biological tissue. For example, the biological tissue can be harvested in sheets that have a width up to about 20 cm, a length of up to about 20 cm, and a thickness of about 0.1 mm to about 3 mm. Conventional techniques can be used for harvesting the biological tissue.

Figure 14:
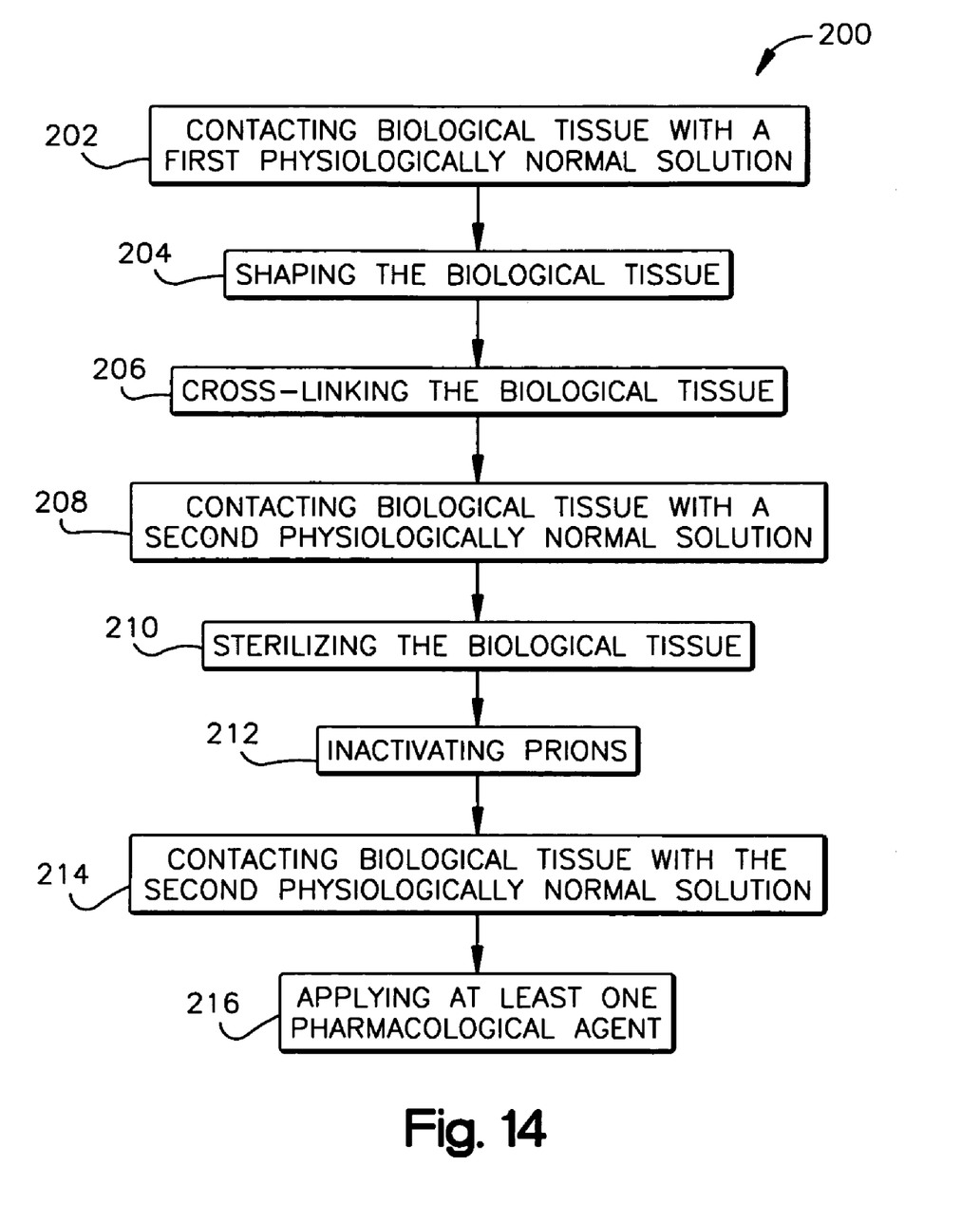
FIG. 14 is a schematic flow diagram of a fixation method in accordance with one aspect of the invention.

In accordance with the present invention, the harvested sheet of biological tissue can be fixed or preserved by a fixation method. FIG. 14 is a flow diagram illustrating a fixation method 200 in which the biological tissue is chemically fixed and sterilized so that the resultant fixed biological tissue contains a plurality of tissue cells. In the fixation method 200, the harvested biological tissue, at 202, is initially contacted or washed with a first physiologically normal solution. The first physiologically normal solution can be a sterile solution comprising saline or distilled water, which is typically used, for example, in irrigating mucous membranes and raw surfaces, in replenishing body water, and/or in restoring blood volume. By way of example, the first physiologically normal solution can have a pH of about 7.4 and can include about 0.9% phosphate buffered saline (PBS) or isotonic saline (e.g., about 0.9% sodium chloride (NaCl) solution).

Following contact with the first physiologically normal solution, at 204, the sheet of biological tissue is shaped by, for example, cutting or trimming the sheet of biological tissue into a desired configuration and then placing the cut or trimmed tissue in the first physiologically normal solution. The desired configuration into which the fixed biological tissue is shaped can depend on the specific application for which the biological tissue is utilized. For example, where the fixed biological tissue is used as a patch, the sheet of biological tissue can be cut or trimmed so that it has a length of about 0.3 cm to about 10 cm and a width of about 6 cm to about 10 cm. Where the biological tissue is used for a tubular graft, the sheet of biological tissue can be cut or trimmed so that it has a length of about 10 cm to about 100 cm and a width of about 2 mm to about 10 cm. Where the fixed biological tissue is used with a tubular stent, the biological tissue can be cut or trimmed so that it has length of about 1 mm to about 100 cm and a width of about 1 mm to about 40 cm.

The cut or trimmed sheet of biological tissue can be placed in the first physiologically normal solution from about 1 hour to about 24 hours. During this time, the first physiologically normal solution can be maintained at a temperature of about 4° C. to about 25° C. For example, the biological tissue may be placed in an about 0.9% PBS (pH 7.4) solution for about 1 hour at about 4° C. after being cut or trimmed.

Optionally, as part of the shaping process, the cut or trimmed biological tissue can also be sutured to a member (e.g., polyethylene plate) prior to placing the cut or trimmed biological tissue in the first physiologically normal solution. Suturing the cut or trimmed biological tissue to the member helps keep the biological tissue in natural form during the fixation process. The member can be flat, curved or dowel shaped, and the shape of the member can depend on the specific application of the fixed biological tissue.

At 206, the shaped biological tissue can be removed from the first physiologically normal solution and at least partially cross-linked by contacting the shaped biological tissue with at least one solution containing at least one cross-linking agent (i.e., cross-linking solution). The cross-linking agent can include an aldehyde, such as glutaraldehyde, formaldehyde, glyceraldehydes, paraformaldehyde, dialdehyde starch, and combinations thereof. Other aldehydes and cross-linking agents, which are typically used to cross-link biological tissue can also be used.

The cross-linking agent can be present in an aqueous solution in a concentration effective to facilitate cross-linking of the biological tissue but not high enough too adversely affect the biological tissue and produce artifacts. This concentration will depend on the particular cross-linking agent used. By way of example, the concentration of glutaraldehyde provided in an aqueous cross-linking solution can range from about 0.625% to about 5.0% by volume.

It will be appreciated that the cross-linking agent solution can include other additives besides the cross-linking agent. These other additives can include, for example, buffers, such as phosphates, bicarbonates, and cacodylates, which can be provided in the cross-linking solution in an amount effective to maintain the cross-linking solution at a pH of about 7 (e.g., about 7.4).

The biological tissue can be cross-linked by contacting the biological tissue with the cross-linking solution for about 2 to about 72 hours. During this time, the cross-linking solution can be maintained at a temperature of about 4° C. to about 25° C. For example, the shaped biological tissue can be contacted with an about 2.5% glutaraldehyde solution for about 1 hour at about 20° C. to about 25° C.

After at least partially cross-linking the biological tissue, at 208, the biological tissue may then be rinsed with a second physiologically normal solution. The second physiologically normal solution, like the first physiologically normal solution, may have a pH of about 7.4 and may include, for example, an about 0.9% PBS or isotonic saline (e.g., about 0.9% NaCl solution).

The at least partially cross-linked sheet of biological tissue can be rinsed with the second physiologically normal solution by placing the biological tissue in the second physiologically normal solution for about 1 hour to about 12 hours. During this time, the second physiologically normal solution can be maintained at a temperature of about 20° C. to about 25° C. For example, the at least partially cross-linked biological tissue can be placed in an about 0.9% PBS (pH 7.4) solution for about 1 hour at a temperature of about 20° C. to about 25° C.

Following rinsing with the second physiologically normal solution, at 210, the at least partially cross-linked biological tissue is contacted with at least one solution containing an alcohol. Contacting the at least partially cross-linked biological tissue with the solution containing alcohol sterilizes the biological tissue and can facilitate further cross-linking of the biological tissue. The solution containing the alcohol can be an aqueous solution and comprise an alcohol, such as ethanol, methanol, propanol, isopropyl alcohol, and combinations thereof. The concentration of alcohol in the solution can range from about 10% to about 90% by volume depending on the particular alcohol utilized. For example, where ethanol is used, it can be provided in the aqueous solution at a concentration of about 50% by volume.

The biological tissue can be contacted with the alcohol containing solution for about 12 hours to about 48 hours to sterilize the biological tissue and promote further cross-linking. The temperature of the alcohol-containing solution during contact with the biological tissue is typically maintained at about 4° C. to about 20° C. By way of example, the biological tissue may be contacted with a 50% ethanol solution for about 24 hours at 20° C. to 25° C.

At 212, the sterilized biological tissue is contacted with a basic or caustic solution that is used to inactivate prions and other infectious and virus related products in the biological tissue. The basic solution can comprise an aqueous solution of at least one base, such as sodium hydroxide (NaOH), potassium hydroxide (KOH), ammonium hydroxide ($NH_4OH$), and combinations thereof.

The molar concentration of basic solution can range from about 0.5 M to about 4.0 M. At a molar concentration less than about 0.5 M, the basic solution can have a strength that is ineffective to inactivate the prions and other infectious and virus related products. At a molar concentration greater than about 4.0 M, the basic solution can have a strength that may potentially damage the biological tissue.

The sterilized biological tissue can be contacted with the basic solution for about 12 hours to about 48 hours to facilitate inactivation of the prions and other infectious and virus related products. The temperature of the basic solution during contact with the biological tissue is typically maintained at about 20° C. to about 25° C. By way of example, the biological tissue may be contacted with a 1 M NaOH solution for about 2 hours at a temperature of about 20° C. to about 25° C.

After inactivation of the prions, at 214, the fixed biological tissue may then be rinsed with the second physiologically normal solution by placing the biological tissue in the second physiologically normal solution for about 1 hour to about 12 hours. During this time, the second physiologically normal solution can be maintained at a temperature of about 20° C. to about 25° C. For example, the biological tissue may be rinsed with the second physiologically normal solution for about 1 hour at about 20° C. to about 25° C.

Following rinsing, the biological tissue may then be placed in a storage solution. The storage solution can comprise, for example, an about 0.625% glutaraldehyde aqueous solution, a 0.9% PBS, isotonic saline (e.g., 0.9% NaCl solution), and combinations thereof. The pH of the storage solution can be about 7.4, and the temperature of the storage solution can be maintained at about 20° C. to about 25° C. For example, the biological tissue may be placed in an about 0.625% glutaraldehyde storage solution at a temperature of about 20° C. to about 25° C. for a period of time less than or equal to about 5 years.

Biological tissue fixed by this method can be used, for example, as a graft that can be positioned within a patient's vasculature. When utilized within a patient's vasculature, the fixed biological tissue is readily endothelized. Ready endothelization of the biological tissue mitigates the formation of clots within the vasculature and promotes biocompatibility of the biological tissue.

It will be appreciated by one skilled in the art that the shaping step, the cross-linking step, the sterilizing step, and the inactivation of prion step need not be performed in the specific order described above but can be performed in any order to obtain a fixed biological tissue that is readily endothelialized. However, by following the sequence of steps described above, other advantages besides ready endothelization of the biological tissue can be obtained. For example, by following the sequence of steps of the present invention, calcification of the biological tissue is inhibited. Additionally, by shaping the biological tissue before cross-linking, the conformation of the biological tissue can more readily be maintained. Further, by cross-linking the biological tissue prior to sterilizing it, bacterial growth on the biological tissue is mitigated.

Figure 15:
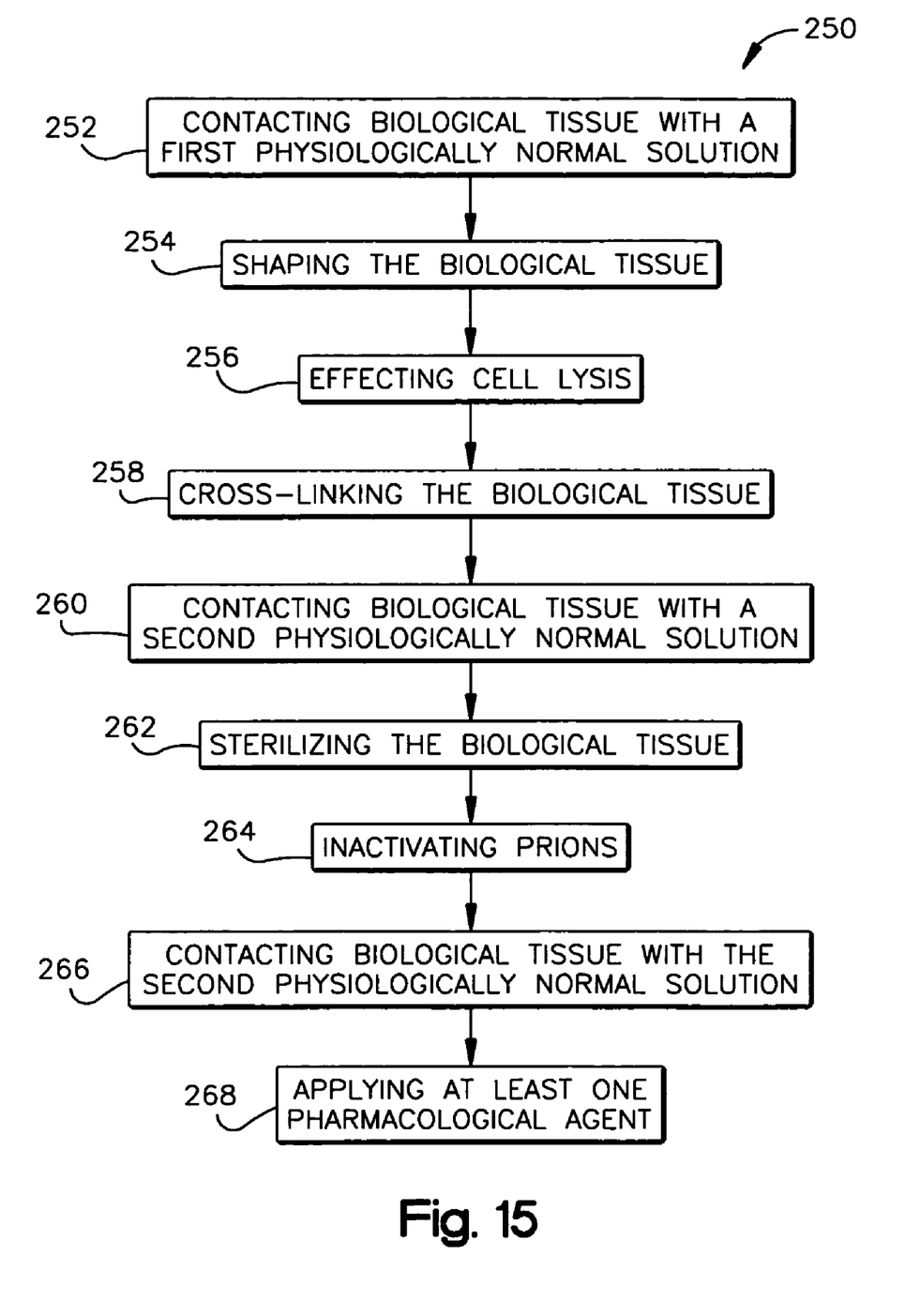
FIG. 15 is a schematic flow diagram of a fixation method in accordance with another aspect of the invention.

FIG. 15 illustrates an alternate fixation method 250 in accordance with the present invention in which the harvested biological tissue is chemically fixed and sterilized so that the resultant fixed biological tissue is acellular. In the fixation method 250, the harvested biological tissue, at 252, is initially contacted or washed with a first physiologically normal solution. The first physiologically normal solution can have a pH of about 7.4 and can include about 0.9% PBS or isotonic saline (e.g., about 0.9% sodium chloride, NaCl solution).

Following contact with the first physiologically normal solution, at 254, the sheet of biological tissue is shaped by, for example, cutting or trimming the sheet of biological tissue into a desired configuration and then placing the cut or trimmed tissue in the first physiologically normal solution. The desired configuration into which the biological tissue is shaped will depend on the specific application for which the biological tissue is utilized.

The cut or trimmed sheet of biological tissue can be placed in the first physiologically normal solution from about 1 hour to about 24 hours. During this time, the first physiologically normal solution can be maintained at a temperature of about 4° C. to about 25° C. For example, the biological tissue may be placed in an about 0.9% PBS (pH 7.4) solution for about 1 hour at about 4° C. after being cut or trimmed.

Optionally, as part of the shaping process, the cut or trimmed biological tissue can also be sutured to a member (e.g., polyethylene plate) prior to placing the cut or trimmed biological tissue in the first physiologically normal solution. Suturing the cut or trimmed biological tissue to the member helps keep the tissue in natural form during the fixation process. The member can be flat, curved or dowel shaped and can depend on the specific application of the fixed biological tissue.

At 256, the shaped biological tissue can be removed from the first physiologically normal solution and placed in at least one solution that can affect cell lysis (i.e., cell lysis solution). A cell lysis solution can include a solution that is hypertonic or has a higher osmotic pressure than the cells of the biological tissue. An example of a cell lysis solution is an aqueous solution that has a solute (e.g., a salt) concentration of about 2% to about 8% by weight of the solution. Lysis of the cells of the biological tissue can be affected by placing the biological tissue in the cell lysis solution for about 2 hours to about 72 hours. The temperature of the cell lysis solution can be maintained at about 4° C. to about 25° C. during cell lysis. By way of example, the biological tissue can be contacted with an about 3% NaCl solution for about 2 hours at a temperature of about 20° C. to about 25° C.

Following cell lysis, the biological tissue may be rinsed in water (e.g., distilled water) for about 1 to about 12 hours. The temperature of the water can be maintained at about 20° C. to about 25° C. during rinsing. For example, the biological tissue can be rinsed in distilled water for about 1 hour at about 20° C. to about 25° C. Thereafter, the biological tissue may be rinsed with the first physiologically normal solution. The biological tissue can be rinsed by placing the biological tissue in the first physiologically normal solution for about 1 to about 12 hours at a temperature of about 20° C. to about 25° C.

At 258, the acellular biological tissue can be removed from the first physiologically normal solution and at least partially cross-linked by contacting the acellular biological tissue with at least one solution containing at least one cross-linking agent (i.e., cross-linking solution). The cross-linking agent can include an aldehyde, such as glutaraldehyde, formaldehyde, glyceraldehydes, paraformaldehyde, dialdehyde starch, and combinations thereof. Other aldehydes and cross-linking agents, which are typically used to cross-link biological tissue, can also be used.

The cross-linking agent can be present in an aqueous solution in a concentration effective to facilitate cross-linking of the biological tissue but not high enough too adversely affect the biological tissue and produce artifacts. This concentration will depend on the particular cross-linking agent used. By way of example, the concentration of glutaraldehyde provided in an aqueous cross-linking solution can range from about 0.625% to about 5.0% by volume.

The acellular biological tissue can be cross-linked by contacting the biological tissue with the cross-linking solution for about 2 to about 72 hours. During this time, the cross-linking solution can be maintained at a temperature of about 4° C. to about 25° C. For example, the acellular biological tissue can be contacted with an about 2.5% glutaraldehyde solution for about 1 hour at about 20° C. to about 25° C.

After at least partially cross-linking the acellular biological tissue, at 260, the at least partially cross-linked acellular biological tissue may then be rinsed with a second physiologically normal solution. The second physiologically normal solution, like the first physiologically normal solution, may have a pH of about 7.4 and may include, for example, an about 0.9% PBS or isotonic saline (i.e., about 0.9% NaCl).

The at least partially cross-linked acellular biological tissue can be rinsed with the second physiologically normal solution by placing the acellular biological tissue in the second physiologically normal solution for about 1 hour to about 12 hours. During this time, the second physiologically normal solution can be maintained at a temperature of about 20° C. to about 25° C. For example, the at least partially cross-linked acellular biological tissue can be placed in an about 0.9% PBS (pH 7.4) solution for about 1 hour at a temperature of about 20° C. to about 25° C.

Following rinsing with the second physiologically normal solution, at 262, the at least partially cross-linked acellular biological tissue is contacted with at least one solution containing an alcohol. Contacting the at least partially cross-linked acellular biological tissue with the solution containing alcohol sterilizes the acellular biological tissue and can facilitate further cross-linking of the acellular biological tissue. The solution containing the alcohol can be an aqueous solution and comprise an alcohol, such as ethanol, methanol, propanol, isopropyl alcohol, and combinations thereof. The concentration of alcohol in the solution can range from about 10% to about 90% by volume depending on the particular alcohol utilized.

The acellular biological tissue can be contacted with the alcohol containing solution for about 12 hours to about 48 hours to sterilize the biological tissue and promote further cross-linking. The temperature of the alcohol-containing solution during contact with the biological tissue is typically maintained at about 4° C. to about 20° C. By way of example, the acellular biological tissue may be contacted with an about 50% ethanol solution for about 24 hours at about 20° C. to about 25° C.

At 264, the sterilized biological tissue is contacted with a basic or caustic solution that is used to inactivate prions and other infectious and virus related products in the acellular biological tissue. The basic solution comprises an aqueous solution of at least one base, such as NaOH, KOH, $NH_4OH$, and combinations thereof.

The molar concentration of basic solution can range from about 0.5 M to about 4.0 M. At a molar concentration less than about 0.5 M, the basic solution can have a strength that is ineffective to inactivate the prions and other infectious and virus related products. At a molar concentration greater than about 4.0 M, the basic solution can have a strength that can potentially damage the acellular biological tissue.

The sterilized acellular biological tissue can be contacted with the basic solution for about 12 hours to about 48 hours to facilitate inactivation of the prions and other infectious and virus related products. The temperature of the basic solution during contact with the acellular biological tissue is typically maintained at about 20° C. to about 25° C. By way of example, the biological tissue can be contacted with a 1M NaOH solution for about 2 hours at a temperature of about 20° C. to about 25° C.

After inactivation of the prions, at 266, the fixed acellular biological tissue may be rinsed with the second physiologically normal solution by placing the fixed acellular biological tissue in the second physiologically normal solution for about 1 hour to about 12 hours. During this time, the second physiologically normal solution can be maintained at a temperature of about 20° C. to about 25° C. For example, the biological tissue may be rinsed with the second physiologically normal solution for about 1 hour at about 20° C. to about 25° C.

Following rinsing, the fixed acellular biological tissue may then be placed in a storage solution. The storage solution can comprise, for example, an about 0.625% glutaraldehyde aqueous solution, a 0.9% PBS, isotonic saline (i.e., 0.9% NaCl), and combinations thereof. The pH of the storage solution can be about 7.4, and the temperature of the storage solution can be maintained at about 20° C. to about 25° C. For example, the fixed acellular biological tissue may be placed in an about 0.625% glutaraldehyde storage solution at a temperature of about 20° C. to about 25° C. for a period of time less than or equal to about 5 years.

As with the biological tissue fixed by the fixation method 200, the acellular biological tissue fixed by the fixation method 250 when utilized within a patient's vasculature is readily endothelized. Ready endothelization of the tissue mitigates the formation of clots within the vasculature and promotes biomcompatibility of the apparatus.

Optionally, as illustrated in FIGS. 14 and 15, after fixing the harvested biological tissue, at least one pharmacological agent can be applied, at 216 and 268, respectively, to the fixed biological tissue (cellular or acellular). The pharmacological agent may be applied to the fixed biological tissue by, for example, coating the fixed biological tissue with pharmacological agent or saturating the fixed biological tissue with the pharmacological agent. Examples of pharmacological agents that be applied to the fixed biological tissue include anticoagulation agents, such as warfarin (COUMADIN), heparin, and lepirudin (REFLUDAN), anti-platelet aggregation agents, such as acetaminophen, ticlopidine (TICLID), clopidogrel (PLAVIX), tirofiban (AGGRASTAT), and eptifibatide (INTEGRILIN), as well as antiproliferative agents and anti-inflammatory agents.

The fixed biological tissue can also be seeded with cells, such as specialized and unspecialized cells (e.g., multipotent adult stem cells). The cells can be genetically modified to express a pharmacological agent or protein that can, for example, facilitate enothelization as well as provide other therapeutic effects (e.g., antiproliferative and anti-inflammatory effects).

Figure 1:
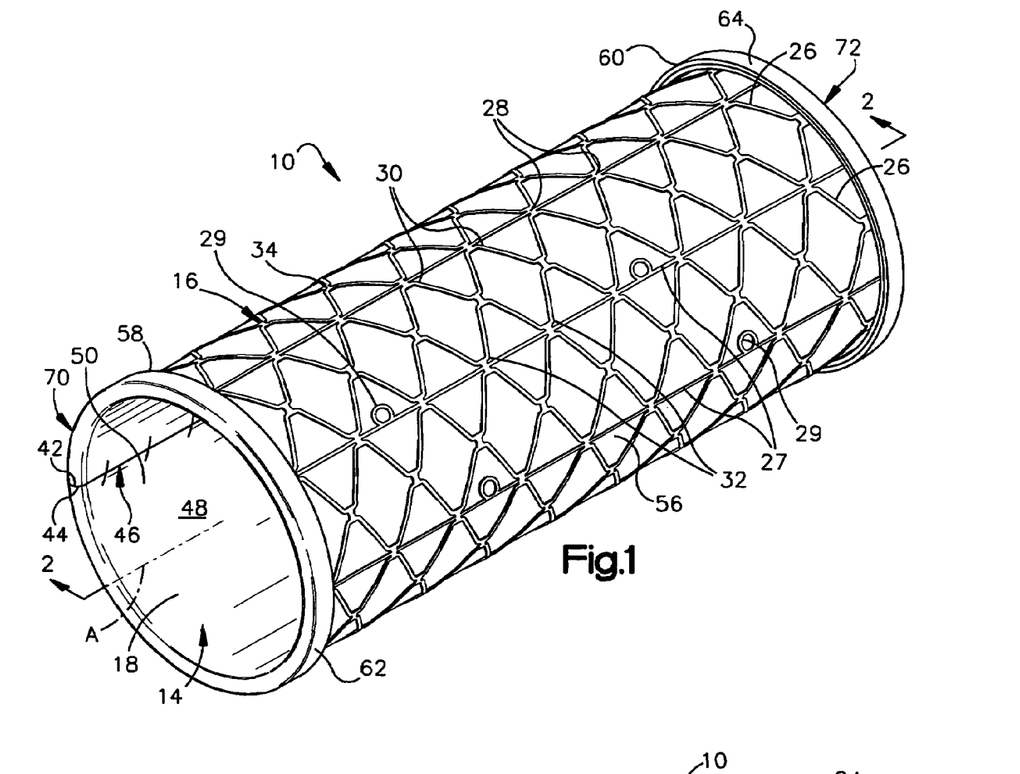
FIG. 1 is a perspective view of an apparatus constructed in accordance with the present invention.
Figure 5:
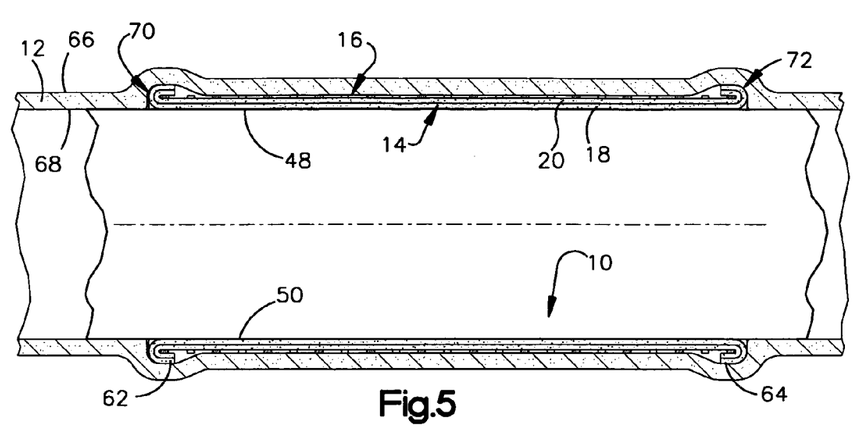
FIG. 5 is a sectional view illustrating the apparatus of FIG. 1 implanted in a blood vessel.

In accordance with another aspect of the present invention, the fixed biological tissue can comprise at least a portion of an apparatus, which can be used for grafting of a blood vessel. FIG. 1 illustrates the apparatus 10 for grafting of a blood vessel 12 (FIG. 5). The apparatus 10 includes a layer of biological tissue 14 fixed by the method of the present invention and an expandable support member 16 (e.g., stent).

Figure 2:
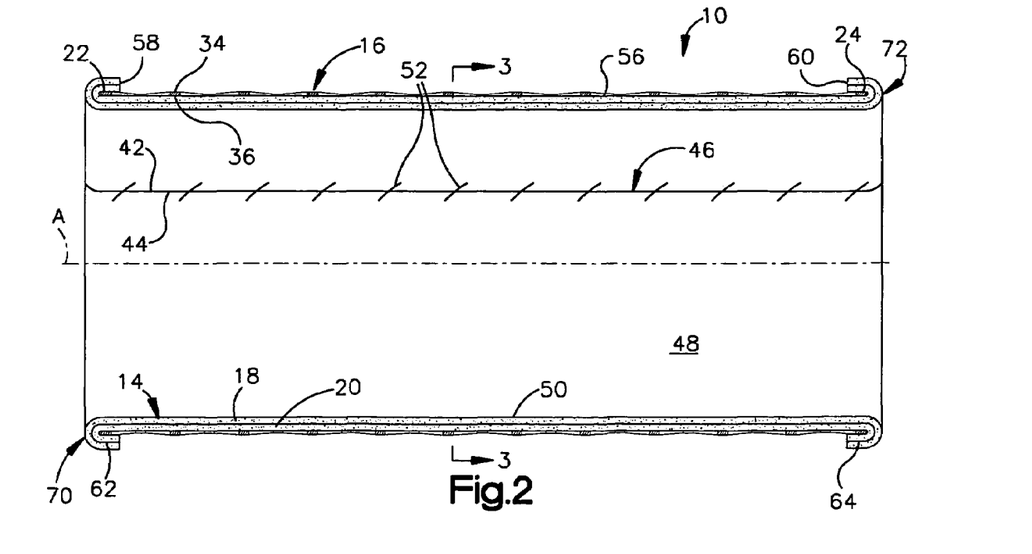
FIG. 2 is a view along line 2-2 in FIG. 1.

Referring to FIG. 2, the expandable support member 16 is tubular and extends axially from a first end 22 to a second end 24. The expandable support member 16 illustrated in FIG. 1 is a mesh structure that includes a plurality of support beams 26 and a plurality of axially extending support rods 27.

Each support beam 26 has a generally sinusoidal shape. The wavelength of each of the support beams 26 is identical or nearly identical to the wavelength of adjacent support beams. Circumferentially adjacent support beams 26 are 180° out of phase from one another. Connector bars 28 (FIG. 1) connect the peaks 30 of each support beam 26 to the associated troughs 32 (FIG. 1) of the adjacent support beam. The amplitude (or height) of each support beam 26 is designed so that a whole number of support beams forms the circumference of the expandable support member 16.

Each of the axially extending support rods 27 extends parallel to axis A. The support rods 27 add additional support to the expandable support member 16. One embodiment of the apparatus 10 includes eight support rods 27 that are equally spaced about the circumference of the expandable support member 16. In the embodiment illustrated in FIG. 1, two support beams 26 are located between adjacent support rods 27.

The expandable support member 16 also includes a plurality of eyelets 29, four of which are shown in FIG. 1. Each eyelet 29 extends from one of the support rods 27. The eyelets 29 illustrated in FIG. 1 are circular, however other shapes may be used. The eyelets 29 provide a means for suturing the layer of biological tissue 14 to the outer support member 16.

The expandable support member 16 is formed from an expandable metal, such as Nitinol. Alternatively, the expandable support may be formed from a fabric layer such as Dacron® or a plastic material such as polytetraflouroethylene (PTFE).

The expandable support member 16 includes an outer surface 34 and an inner surface 36 (FIG. 2). The outer surface 34 is generally cylindrical and extends axially along axis A. The inner surface 36 is also generally cylindrical and is coaxial with the outer surface 34.

Alternatively, the expandable support member 16 may include any known stent structure that is expandable and that defines inner and outer surfaces 36 and 34, respectively. Although the apparatus 10 is illustrated as being cylindrical with a circular cross-sectional shape, the cross-sectional shape of the apparatus may alternatively be elliptical, polygonal, or cone-shaped.

Figure 4A:
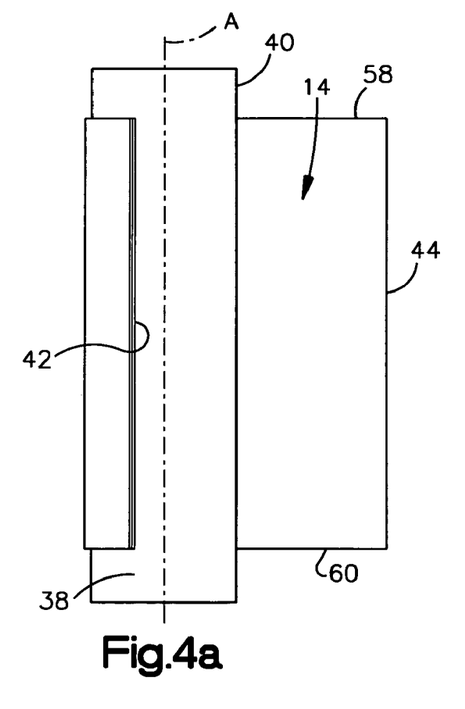
FIGS. 4a-4f illustrate the method of forming the apparatus of FIG. 1.

FIGS. 4a-4f illustrate a method for forming the apparatus 10 of the present invention. The method begins at FIG. 4a with a dowel 38 and a sheet of biological tissue 14 that has been fixed and trimmed into a rectangular shape. The dowel 38 is formed from glass. The dowel 38 illustrated in FIG. 4a is cylindrical and has an outer surface 40 with a circular cross-sectional shape. Alternatively, the dowel 38 may be cone-shaped. A circumference of the outer surface 40 of the dowel 38 is equal to a width of the biological tissue 14. The width of the biological tissue 14 is defined as the distance between a first side surface 42 and a second side surface 44. FIG. 4a illustrates the biological tissue 14 being wrapped or rolled around the dowel 38.

Figure 4B:
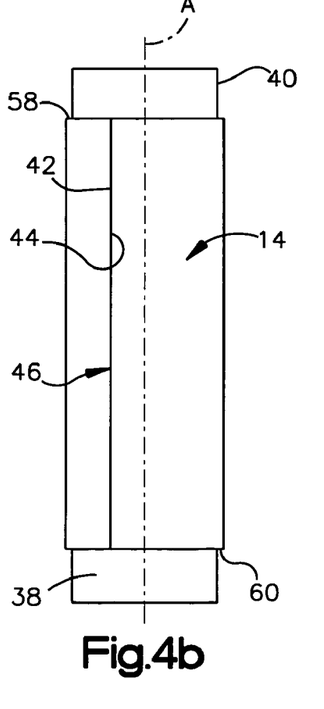

FIG. 4b illustrates the biological tissue 14 completely wrapped around the dowel 38. When completely wrapped around the dowel 38, the first side surface 42 of the biological tissue 14 abuts, rather than overlaps, the second side surface 44 of the biological tissue 14. An axially extending seam 46 is defined at the location where the first side surface 42 and the second side surface 44 meet. The seam 46 extends along an axial length of the biological tissue 14. The axial length of the biological tissue 14 is defined as a distance between a first axial end 58 and a second axial end 60.

The first side surface 42 abuts the second side surface 44 such that the inner surface 48 (FIGS. 1-3) of the apparatus 10, which is defined by an inner surface 50 (FIGS. 1-3) of an inner lining 18 of the biological tissue 14, is smooth, continuous, and uninterrupted. Since the inner surface 48 of the apparatus 10 has no projections or irregularities, such as would be present if the biological tissue 14 were overlapped, thrombosis and platelet deposition at the seam 46 are resisted. An additional benefit of abutting the first and second side surfaces 42 and 44 of the biological tissue 14 together is that the smooth, continuous, and uninterrupted inner surface 48 of the apparatus 10 does not create turbulent flow through the apparatus.

Figures 4C, 4D:
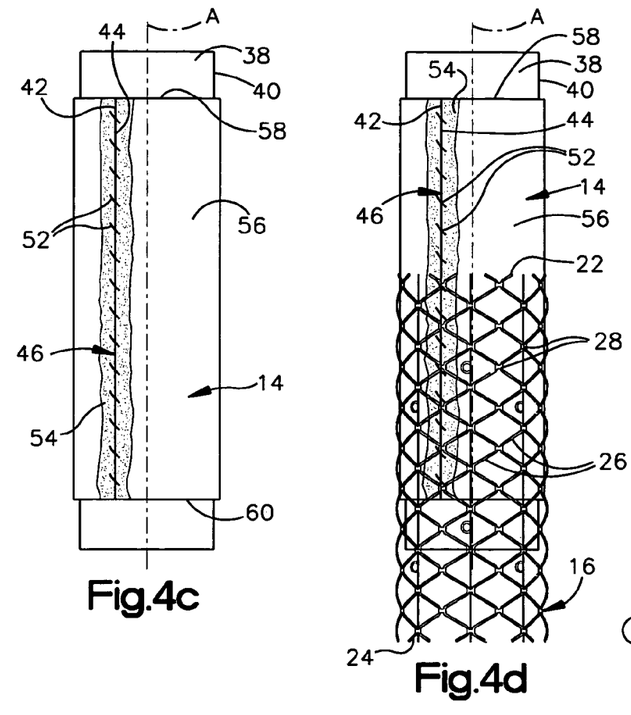

In FIG. 4c, the first side surface 42 of the biological tissue 14 is attached to the second side surface 44 of the biological tissue 14 using sutures 52. The sutures 52 extend radially inwardly through the biological tissue 14 and generally circumferentially between areas adjacent the first and second side surfaces 42 and 44. The biological tissue 14 remains on the dowel 38 while the sutures 52 are sewn in place. A layer of biological glue 54 may be placed over the seam 46 on an outer surface 56 of the biological tissue 14. The biological glue 54 helps to ensure that the inner surface 48 of the apparatus 10 remains smooth, continuous, and uninterrupted. The biological glue 54 also aids in completely sealing the seam 46 to prevent any leakage through the seam 46.

FIG. 4d illustrates the expandable support member 16 being placed over the biological tissue 14. The expandable support member 16 forms an outer support for the biological tissue 14. The expandable support member 16 forms the radially outermost component of the apparatus 10. The radially innermost component of the apparatus 10 is formed by the serous membrane lining 18 of the layer of biological tissue 14.

To place the expandable support member 16 over the biological tissue 14, the expandable support member 16 is expanded. Any known method for expanding the expandable support member 16 may be used, such as heating or balloon dilation of the expandable support member. The dowel 38 and the biological tissue 14 that is being held on the dowel 38 are inserted into the first end 22 of the expandable support member 16, as shown in FIG. 4d. The expandable support member 16 and the dowel 38 are moved relative to one another until an equivalent amount of biological tissue 14 extends axially outwardly of both the first and second ends 22 and 24 of the expandable support member 16.

The expandable support member 16 is then constricted until the inner surface 36 of the expandable support member 16 engages the outer surface 56 of the biological tissue 14 equally about the circumference of the outer surface 56 of the biological tissue 14. Next, the biological tissue 14 is attached to the expandable support member 16. Preferably, sutures (not shown) are used to attach the biological tissue 14 to the expandable support member 16. Each suture extends through the biological tissue 14 and a portion of the suture is threaded through one of the eyelets 29 of the expandable support member 16. The suture is then tied outside of the expandable support member 16 and around the respective eyelet 29. The suture holds the biological tissue 14 to the inner surface 36 of the expandable support member 16. The sutures are sufficiently small so that turbulent flow will not result from the interaction of blood flow with the sutures. Alternately, the outer surface 56 of the biological tissue 14 may be glued to the inner surface 36 of the expandable support member 16 using biological glue. When biological glue is used to attach the biological tissue 14 to the expandable support member 16, the support beams 26 and the support rods 27 must have an inner surface area large enough for adhesion of the biological tissue 14.

Figure 4E:
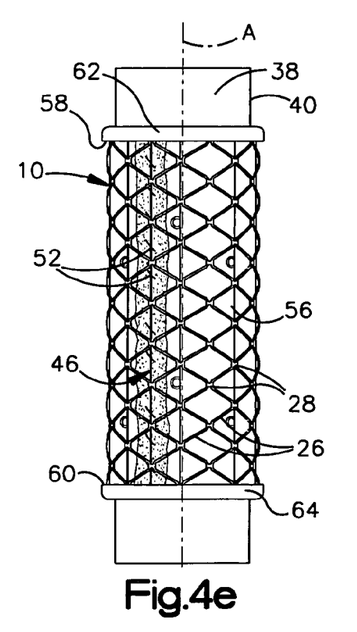

After the biological tissue 14 is attached to the expandable support member 16, the first and second axial ends 58 and 60 of the biological tissue 14 are folded over the first and second ends 22 and 24, respectively, of the expandable support member 16, as is shown in FIG. 4e. The first axial end 58 of the biological tissue 14 is stretched and folded over the first end 22 of the expandable support member 16 to form a first folded portion 62. The first folded portion 62 is then attached to the outer surface 34 of the expandable support member 16 using sutures (not shown). A second axial end 60 of the biological tissue 14 is stretched and folded over the second end 24 of the expandable support member 16 to form a second folded portion 64. The second folded portion 64 is also attached to the expandable support member 16 using sutures (not shown).

Figure 4F:
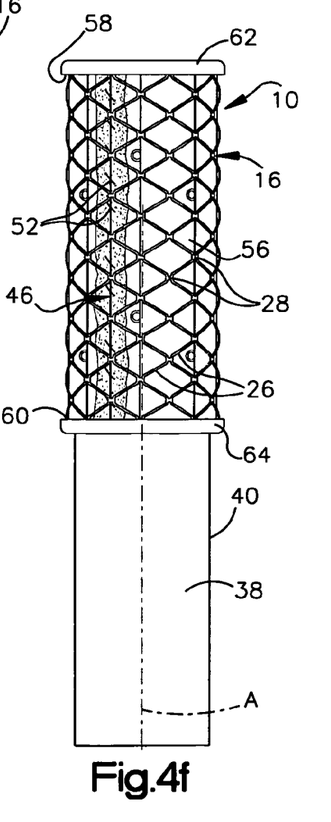

The apparatus 10, including the dowel 38, is stored in a sterile environment until it is time for implantation into a patient. Preferably, the apparatus 10 is submersed in a biological solution and is stored in a sterile, vacuum-packed container (not shown). Alternatively, the dowel 38 may be removed from the apparatus 10 prior to storing the apparatus. FIG. 4f illustrates the dowel 38 being removed from the apparatus 10. Preferably, the dowel 38 and the apparatus 10 are placed in biological or fixing solution to facilitate removal of the dowel 38 from inside the apparatus 10. The solution will sufficiently lubricate the dowel 38 and the biological tissue 14 so that the dowel may be removed from the apparatus 10 without tearing or weakening the biological tissue 14. As a result, the inner surface 48 of the apparatus 10 remains smooth, continuous, and uninterrupted. Alternatively, the apparatus 10 may be expanded and the dowel 38 removed from the expanded apparatus 10.

FIG. 5 illustrates the apparatus 10 of the present invention implanted in a blood vessel 12. The blood vessel 12 includes an outside surface 66 and an inside surface 68. The inside surface 68 of the blood vessel 12 forms a conduit for directing blood flow. The apparatus 10 is delivered and positioned in the blood vessel 12 using methods that are known in the art. Once the apparatus 10 is positioned in the desired location in the blood vessel 12, the expandable support member 16 is expanded, by a balloon (not shown) or through self-expansion as is known in the art. When the expandable support member 16 expands, a first end 70 of the apparatus 10 engages the blood vessel 12 such that an interference fit is created between the first folded portion 62 and the inside surface 68 of the blood vessel 12. Similarly, a second end 72 of the apparatus 10 engages the blood vessel 12 such that an interference fit is created between the second folded portion 64 and the inside surface 68 of the blood vessel 12. An interference fit is also created between the expandable support member 16 and the inner surface 68 of the blood vessel 12 along the axial length of the apparatus 10 that extends between the first and second ends 70 and 72. In addition to the interference fit between the expandable support member 16 and the blood vessel 12, sutures can also used to anchor the expandable support member 16 to the blood vessel 12.

When the apparatus 10 engages and adheres to the inside surface 68 of the blood vessel 12 in the above manner, the inner lining 18 of serous membrane forms the outermost surface at the first and second folded portions 62 and 64. The inner lining 18 bonds to the inside surface 68 of the blood vessel 12 in a normal tissue-healing fashion and prevents the ingrowth of inflammatory tissue. As a result, the bond between the serous membrane of the inner lining 18 at the first and second folded portions 62 and 64 and the inside surface 68 of the blood vessel 12 prevents restenosis or occlusion. Additionally, the healing bond between the serous membrane of the inner lining 18 at the first and second folded portions 62 and 64 and the inside surface 68 of the blood vessel 12 forms more quickly than a bond between a fascia lining 20 and the inside surface 68 of the blood vessel 12.

When implanted in the blood vessel 12, the conduit formed by the inner surface 50 of the biological tissue 14 is confluent with the inside surface 68 of the blood vessel 12. The transition between the inside surface 68 of the blood vessel 12 and the inner surface 50 of the biological tissue 14 is smooth so that thrombosis and platelet deposition is resisted and that blood flow is not restricted when passing through the apparatus 10. The expandable support member 16 provides sufficient support against the internal pressure caused by the blood flow through the apparatus 10, and also resists radial collapse of the blood vessel.

Figure 6:
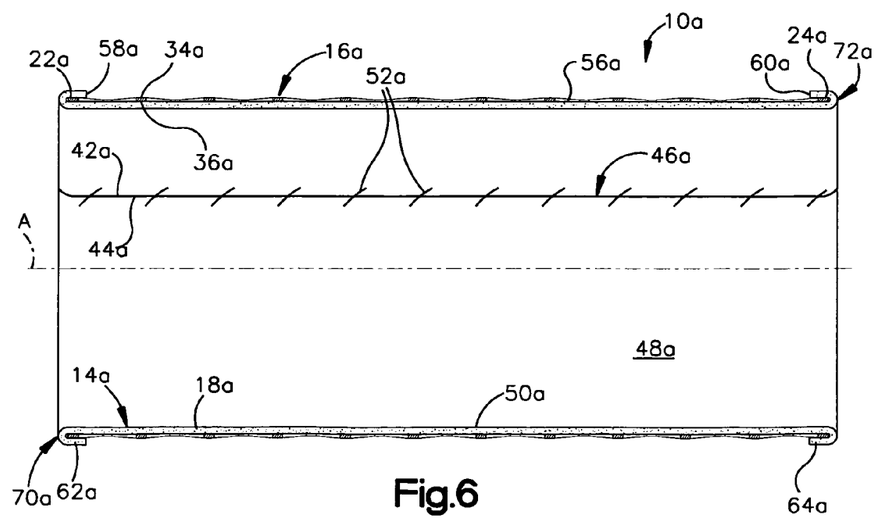
FIG. 6 is a longitudinal sectional view of a second embodiment of an apparatus constructed in accordance with the present invention.

FIG. 6 is a longitudinal sectional view of a second embodiment of an apparatus 10a constructed in accordance with the present invention. Structures of the embodiment shown in FIG. 6 that are similar to structures of FIGS. 1-3 have the same reference numbers with the suffix "a" added. The apparatus 10a is identical to apparatus 10 of FIGS. 1-3 with the exception that the layer of biological tissue 14a in the embodiment of FIG. 6 includes only a layer 18a of serous membrane.

The layer of biological tissue 14a is harvested to include only the layer 18a of serous membrane. The method for harvesting only a layer 18a of serous membrane is known in the art.

The assembly of apparatus 10a is identical to the assembly of apparatus 10 that is illustrated in FIGS. 4a-4f. When trimmed into the desired shape, the layer of biological tissue 14a includes first and second side surfaces 42a and 44a, respectively, and first and second axial ends 58a and 60a, respectively.

The assembled apparatus includes a seam 46a that is formed from abutting the first and second side surfaces 42a and 44a. The assembled apparatus 10a also includes first and second folded portions 62a and 64a. The first folded portion 62a is formed by folding the first axial end 58a of the layer of biological tissue 14a over the first end 22a of the expandable support member 16a. The second folded portion 64a is formed by folding the second axial end 60a of the layer of biological tissue 14a over the second end 24a of the expandable support member 16a.

The inner surface 48a of the assembled apparatus 10a is defined by the inner surface 50a of the layer 18a of serous membrane. The inner surface 148a of the apparatus 10a is smooth, continuous, and uninterrupted. The smooth, continuous, and uninterrupted inner surface 48a of the apparatus 10a resists thrombosis and platelet deposition.

Figure 7:
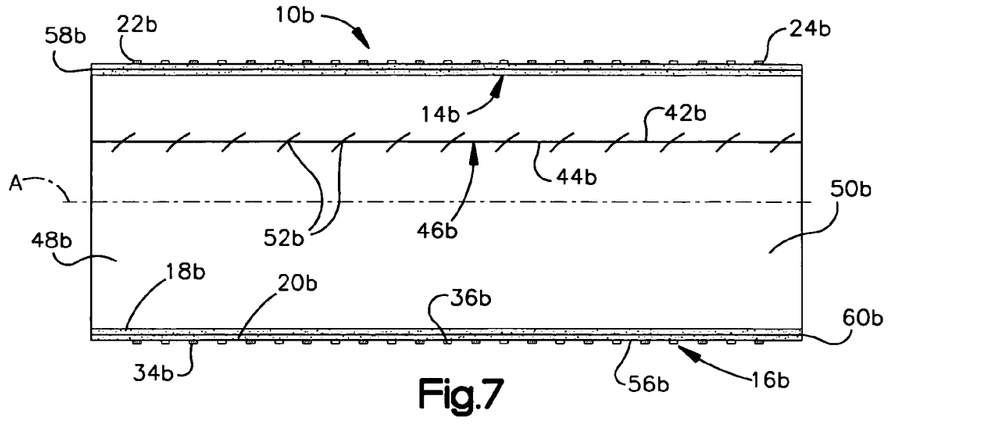
FIG. 7 is a longitudinal sectional view of a third embodiment of an apparatus constructed in accordance with the present invention.

FIG. 7 is a longitudinal sectional view of an apparatus 10b constructed in accordance with a third embodiment of the present invention. Structures of the embodiment shown in FIG. 7 that are similar to structures of FIGS. 1-3 have the same reference numbers with the suffix "b" added.

The apparatus 10b illustrated in FIG. 7 includes a layer of biological tissue 14b and an expandable support member 16b. The layer of biological tissue 14b includes a serous membrane lining 18b and associated fascia lining 20b. The expandable support member 16b has a structure similar to that illustrated in FIG. 1. The layer of biological tissue 14b forms the innermost component of the apparatus 10b.

The layer is biological tissue 14b is formed into a tubular portion by abutting first and second side surfaces 42b and 44b of the biological tissue 14b at a seam 46b. Preferably, the first and second side surfaces 42b and 44b are sutured together at the seam 46b and biological glue (not shown) is applied to an outer surface 56b of the biological tissue 14b.

The outer surface 56b of the layer of biological tissue 14b is attached to the inner surface 36b of the expandable support member 16b. The expandable support member 16b is placed over the biological tissue 14b such that equal amounts of biological tissue 14b extend from the first and second ends 22b and 24b of the expandable support member 16b. Instead of folding the first and second axial ends 58b and 60b of the biological tissue 14b over the expandable support member 16b as discussed above with regard to the embodiment of FIGS. 1-3, the first and second axial ends 58b and 60b of the biological tissue 14b extend axially beyond the first and second ends 22b and 24b of the expandable support member 16b. Thus, in assembling the apparatus 10b, the step illustrated in FIG. 4e is omitted.

When implanted into a blood vessel of a patient, the first and second axial ends 58b and 60b of the tissue 14b engage and are adhered to the inside surface of the blood vessel by the expansion of the expandable support member 16. The extension of the first and second axial ends 58b and 60b of the biological tissue 14b axially beyond the first and second ends 22b and 24b of the expandable support member 16b allows the first and second axial ends of the biological tissue to be sutured directly to the inside surface of the blood vessel.

Figure 8:
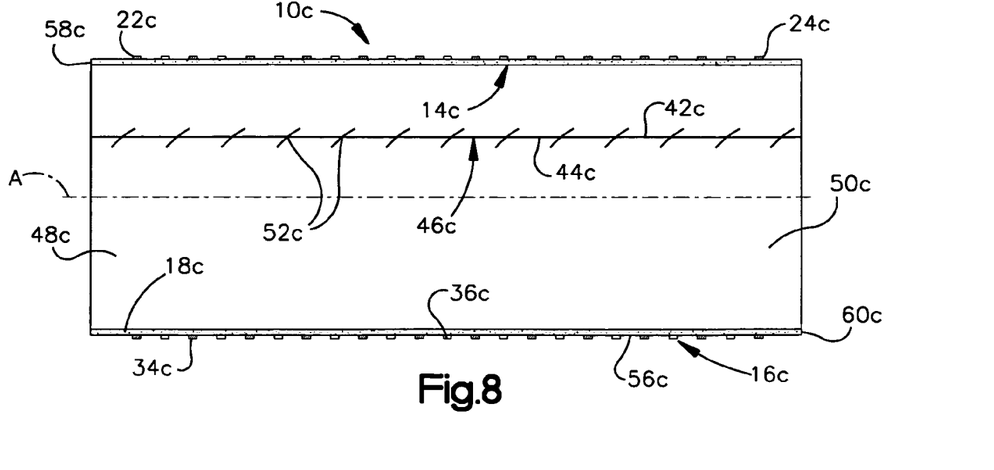
FIG. 8 is a longitudinal sectional view of a fourth embodiment of an apparatus constructed in accordance with the present invention.

FIG. 8 is a longitudinal sectional view of a fourth embodiment of an apparatus 10c constructed in accordance with the present invention. Structures of the embodiment shown in FIG. 8 that are similar to structures of FIG. 7 have the same reference numbers with the suffix "c" replacing the suffix "b". The apparatus 10c is identical to apparatus 10b of FIG. 7 with the exception that the layer of biological tissue 14c in the embodiment of FIG. 8 includes only a layer 18c of serous membrane.

The assembly of apparatus 10c is identical to the assembly of apparatus 10b. When trimmed into the desired shape, the layer of biological tissue 14c includes first and second side surfaces 42c and 44c, respectively, and first and second axial ends 58c and 60c, respectively.

The assembled apparatus includes a seam 46c that is formed from abutting the first and second side surfaces 42c and 44c. The inner surface 48c of the assembled apparatus 10c is defined by the inner surface 50c of the layer 18c of serous membrane. The inner surface 48c of the apparatus 10c is smooth, continuous, and uninterrupted. The smooth, continuous, and uninterrupted inner surface 48c of the apparatus 10c resists thrombosis and platelet deposition.

Figure 9:
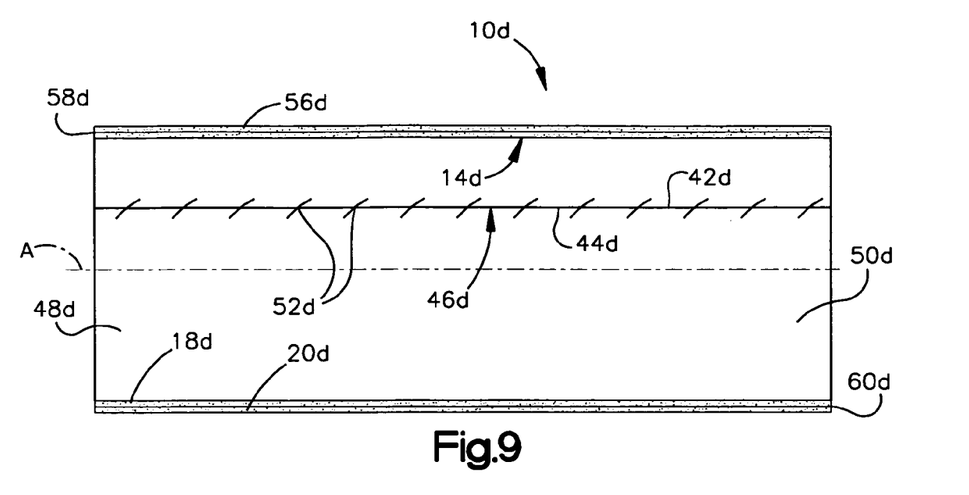
FIG. 9 is a longitudinal sectional view of a fifth embodiment of an apparatus constructed in accordance with the present invention.

FIG. 9 illustrates a longitudinal sectional view of a fifth embodiment of an apparatus 10d constructed in accordance with the present invention. Structures of the embodiment shown in FIG. 9 that are similar to structures of FIG. 7 have the same reference numbers with the suffix "d" replacing the suffix "b".

The apparatus 10d of FIG. 9 is also a cardiovascular graft. The apparatus 10d includes a layer of biological tissue 14d that includes an inner lining 18d of serous membrane and an outer lining 20d of fascia associated with the serous membrane. The layer of biological tissue 14d is rectangular and includes first and second side surfaces 42d and 44d, respectively, and first and second axial ends 58d and 60d, respectively. The inner lining 18d of serous membrane includes an inner surface 50d. The outer lining 20d of fascia includes an outer surface 56d.

The apparatus 10d illustrated in FIG. 9 is cylindrical and is formed by the layer of biological tissue 14d. The first and second side surfaces 42d and 44d of the layer of biological tissue 14d are abutted and secured together to define a seam 46d. Sutures 52d attach the first and second side surfaces 42d and 44d at the seam 46d. A layer of biological glue (not shown) is applied to the outer surface 56d of the outer lining 20d over the seam 46d. The biological glue aids in completely sealing the seam 46d to prevent any leakage through the seam.

Figure 3:
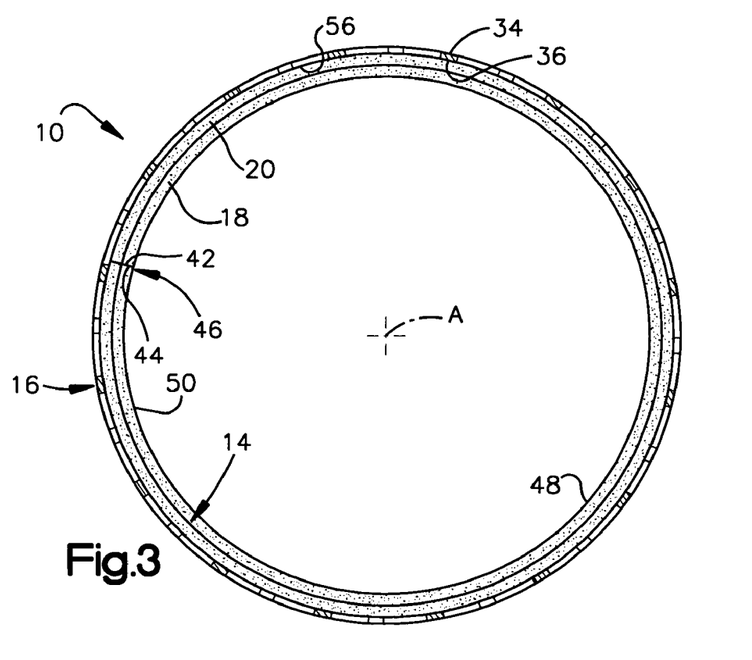
FIG. 3 is a view along line 3-3 in FIG. 2.

To form the apparatus 10d, the steps illustrated in FIGS. 4a to 4c and discussed in detail with regards to apparatus 10 of FIGS. 1-3 are followed. After the step shown in FIG. 4c, the apparatus 10d is stored in a sterile environment until it is time for implantation into a patient. Prior to implantation into the patient, the dowel is removed from the apparatus.

The outer surface 56d of the outer lining 20d forms the outermost component of the apparatus 10d. The inner surface 50d of the inner lining 18d of serous membrane forms the innermost component of the apparatus 10d. The inner surface 50d of the inner lining 18d is smooth, continuous, and uninterrupted. As a result, the inner surface 48d of the apparatus 10*d* is smooth, continuous, and uninterrupted and resists thrombosis and platelet deposition.

When surgically implanted in a patient, the apparatus 10*d* is attached using sutures. For example, when used within a blood vessel, the apparatus 10*d* is sutured to the inside surface of the blood vessel. As a result, the continuous and uninterrupted inner surface 50*d* of the inner lining 18*d* is confluent with the inside surface of the blood vessel.

Since the apparatus 10*d* includes no support structures, the apparatus adapts or conforms to the shape of the blood vessel into which it is attached. Thus, if the inside surface of the blood vessel has an elliptical cross-sectional shape, the apparatus 10*d*, when attached to the inside surface of the blood vessel, has an elliptical cross-sectional shape.

Figure 10:
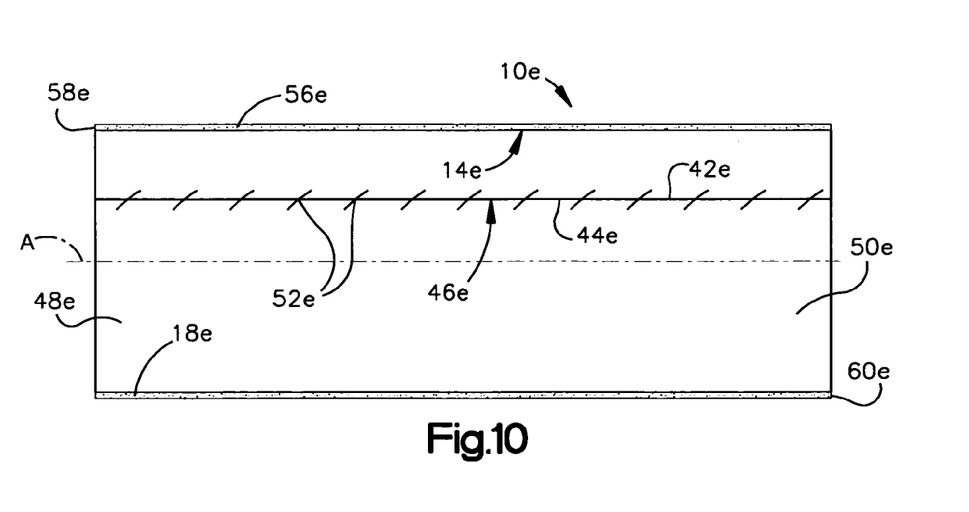
FIG. 10 is a longitudinal sectional view of a sixth embodiment of an apparatus constructed in accordance with the present invention.

FIG. 10 is a longitudinal sectional view of a sixth embodiment of an apparatus 10*e* constructed in accordance with the present invention. Structures of the embodiment shown in FIG. 10 that are similar to structures of FIG. 9 have the same reference numbers with the suffix "e" replacing the suffix "d". The apparatus 10*e* is identical to apparatus 10*d* of FIG. 9 with the exception that the layer of biological tissue 14*e* in the embodiment of FIG. 10 includes only a layer 18*e* of serous membrane.

The assembly of apparatus 10*e* is identical to the assembly of apparatus 10*e*. When trimmed into the desired shape, the layer of biological tissue 14*e* includes first and second side surfaces 42*e* and 44*e*, respectively, and first and second axial ends 58*e* and 60*e*, respectively.

The assembled apparatus includes a seam 46*e* that is formed from abutting the first and second side surfaces 42*e* and 44*e*. The inner surface 48*e* of the assembled apparatus 10*e* is defined by the inner surface 50*e* of the layer 18*e* of serous membrane. The inner surface 48*e* of the apparatus 10*e* is smooth, continuous, and uninterrupted. The smooth, continuous, and uninterrupted inner surface 48*e* of the apparatus 10*e* resists thrombosis and platelet deposition.

Figure 11:
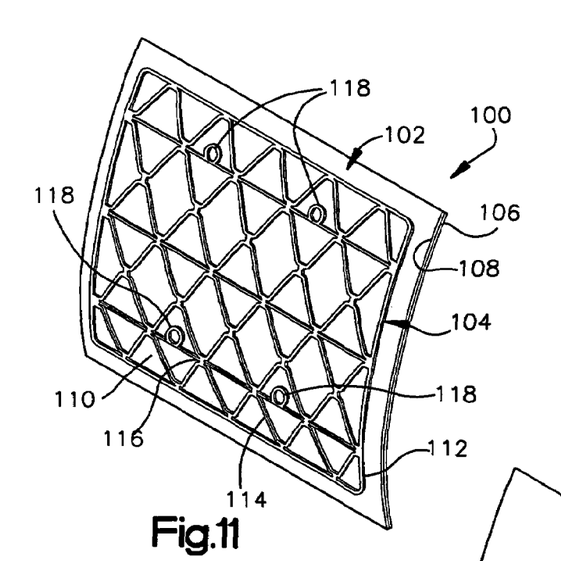
FIG. 11 is a perspective view of a seventh embodiment of an apparatus constructed in accordance with the present invention.

FIG. 11 illustrates a perspective view of a seventh embodiment of an apparatus 100 constructed in accordance with the present invention. The apparatus 100 in FIG. 11 is a patch for repairing a portion of a blood vessel or other membrane within the cardiovascular system of the human body.

The patch 100 includes a layer of biological tissue 102 and an outer support member 104. The layer of biological tissue 102 includes a serous membrane lining 106 and associated fascia lining 108. The serous membrane lining 106 forms an inner surface (not shown) of the biological tissue 102 and the associated fascia 108 forms an outer surface 110 of the biological tissue 102. The layer of biological tissue 102 is illustrated as being rectangular but may be of any desired shape.

The outer support member 104 has the same shape as the biological tissue 102 but is slightly smaller is size. The outer support member 104 may have a curved profile, as is illustrated in FIG. 11, for fitting to a curved surface such as the inside or outside surfaces of a blood vessel.

The outer support member 104 in FIG. 11 is rectangular and includes an outer frame 112 and inner support beams 114. The outer frame 112 defines the shape of the outer support member 104 and provides support near the periphery of the biological tissue 102. The inner support beams 114 of the outer support member 104 provide support for an interior portion of the biological tissue 102. Eyelets 118 are provided through which sutures (not shown) may be threaded when attaching the biological tissue 102 to the outer support member 104.

The outer surface 110 of the biological tissue 102 is attached to the outer support member 104. Preferably, the biological tissue 102 is sutured to the outer support member 104. The peripheral portion of the biological tissue 102 extends outwardly from the outer support member 104. Alternatively, the peripheral portion of the biological tissue 102 may be folded over the outer frame 112 of the outer support member 104.

When implanted in a blood vessel, an outer surface 116 of the outer support member 104 of the patch 100 is placed over an aneurysm or a weakened portion of the blood vessel. The size of the outer support member 104 is preferably larger than the aneurysm or weakened portion of the blood vessel such that the outer frame 112 of the outer support member 104 contacts healthy portions of the inside surface of the blood vessel. The outer periphery of the biological tissue 102 is then attached to the inside surface of the blood vessel, preferably by suturing. The patch 100 may alternatively be placed over the outside surface of the blood vessel or be used on another membrane of the cardiovascular system.

Figure 12:
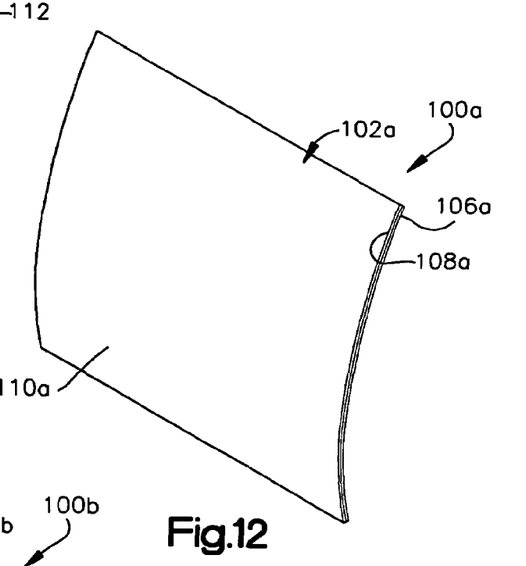
FIG. 12 is a perspective view of an eighth embodiment of an apparatus constructed in accordance with the present invention.

FIG. 12 is a view of an eighth embodiment of an apparatus 100*a* constructed in accordance with the present invention. Structures of the embodiment shown in FIG. 12 that are similar to structures of FIG. 11 have the same reference numbers with the suffix "a" added.

The apparatus 100*a* of FIG. 12 is also a patch for repairing a portion of a blood vessel or other membrane within the cardiovascular system of the human body. The patch 100*a* includes a layer of biological tissue 102*a*. The patch 100*a* of FIG. 12 does not include a support structure such as the outer support structure 104 illustrated in FIG. 11.

The layer of biological tissue 102*a* includes a serous membrane lining 106*a* and associated fascia lining 108*a*. The serous membrane lining 106*a* forms an inner surface (not shown) of the biological tissue 102*a* and the associated fascia 108*a* forms an outer surface 110*a* of the biological tissue 102*a*. The inner surface of the biological tissue 102*a* is smooth, continuous, and uninterrupted. The layer of biological tissue 102*a* is illustrated as being rectangular but may be of any desired shape.

When implanted in a blood vessel, an outer surface 110*a* of the associated fascia 108*a* of the layer of biological tissue 102*a* is placed over an aneurysm or a weakened portion of the blood vessel. The biological tissue 102*a* is then attached to the inside surface of the blood vessel, preferably by suturing. Since the patch 100*a* does not include structural support, the patch 100*a* easily adapts to the shape of the blood vessel or membrane to which it is attached to ensure a sufficient area of contact between patch 100*a* and the blood vessel or membrane. The patch 100*a* may alternatively be placed over the outside surface of the blood vessel or be used on another membrane of the cardiovascular system.

Figure 13:
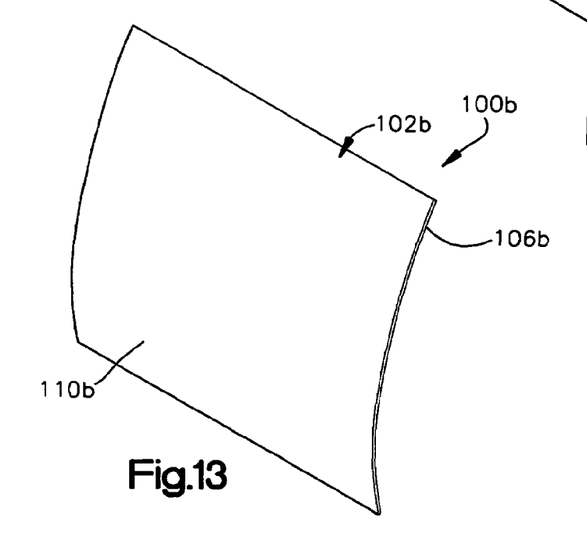
FIG. 13 is a perspective view of a ninth embodiment of an apparatus constructed in accordance with the present invention.

FIG. 13 is a perspective view of a ninth embodiment of an apparatus 100*b* constructed in accordance with the present invention. Structures of the embodiment shown in FIG. 13 that are similar to structures of FIG. 12 have the same reference numbers with the suffix "b" replacing the suffix "a". The apparatus 100*b* is identical to apparatus 100*a* of FIG. 12 with the exception that the layer of biological tissue 102*b* in the embodiment of FIG. 13 includes only a layer 106*b* of serous membrane.

The outer surface 110*b* of the biological tissue 102*b* is formed by an outer surface of the layer 106*b* of serous membrane. The inner surface (not shown) of the biological tissue is formed by an inner surface of the layer 106*b* of serous membrane and is smooth, continuous and uninterrupted.

From the above description of the invention, those skilled in the art will perceive improvements, changes and modifications. For example, it is contemplated that the biological tissue 14 fixed by the methods described herein could be used Having described the invention, I claim:

1. A method of preparing a fixed biological tissue, the method comprising:
   (a) harvesting at least one layer of biological tissue, the biological tissue being selected from the group consisting of pericardial tissue, peritoneal tissue, and pleural tissue, the layer of biological tissue comprising an inner lining of a serous membrane and an outer lining of associated fascia;
   (b) shaping the biological tissue, wherein the shaping comprises trimming and shaping the harvested layer of biological tissue to a desired size and configuration;
   (c) at least partially cross-linking the biological tissue by contacting the biological tissue with a solution containing at least one cross-linking agent;
   (d) sterilizing the biological tissue by contacting the at least partially cross-linked biological tissue with a solution containing an alcohol; and
   (e) inactivating prions in the sterilized biological tissue, the prions in the biological tissue being inactivated by contacting the sterilized biological tissue with a basic solution having a molar concentration of about 0.5 M to about 4.0 M;
   whereby steps (a)-(e) are performed sequentially.

2. The method of claim 1, further comprising suturing the cut biological tissue to a member.

3. The method of claim 1, the cross-linking agent being selected from the group consisting of glutaraldehyde, formaldehyde, glyceraldehyde, paraformaldehyde, dialdehyde starch, and combinations thereof.

4. The method of claim 1, the alcohol being selected from the group consisting of ethanol, methanol, propanol, isopropanol, and combinations thereof and being present in the solution at a concentration of about 10% to about 90% by volume.

5. The method of claim 1, further comprising contacting the biological tissue with at least one solution that causes lysis of cells of the biological tissue.

6. The method of claim 5, the solution that causes cell lysis being a hypertonic solution that has a salt concentration of about 2% to about 8% by weight.

7. The method of claim 1, further comprising applying at least one pharmacological agent to the biological tissue, the at least one pharmacological agent being selected from the group consisting of an anti-inflammatory agent, an anti-proliferative agent, an anti-coagulation agent, or an anti-platelet aggregation agent.

8. A method of preparing a fixed biological tissue, the method comprising:
   (a) harvesting at least one layer of biological tissue, the biological tissue being selected from the group consisting of pericardial tissue, peritoneal tissue, and pleural tissue, the layer of biological tissue comprising an inner lining of a serous membrane and an outer lining of associated fascia;
   (b) shaping the layer of harvested biological tissue, wherein the shaping comprises trimming and shaping the harvested layer of biological tissue to a desired size and configuration;
   (c) at least partially cross-linking the shaped biological tissue by contacting the biological tissue with a solution containing at least one cross-linking agent;
   (d) sterilizing the at least partially cross-linked biological tissue by contacting the biological tissue with a solution containing an alcohol; and
   (e) inactivating prions in the sterilized biological tissue, the prions in the biological tissue being inactivated by contacting the sterilized biological tissue with a basic solution having a molar concentration of about 0.5 M to about 4.0 M;
   whereby steps (a)-(e) are performed sequentially.

9. The method of claim 8, further comprising applying at least one pharmacological agent to the fixed biological tissue, the pharmacological agent comprising at least one of an anti-inflammatory agent, an anti-proliferative agent, an anti-coagulation agent, or an anti-platelet aggregation agent.

10. The method of claim 8, further comprising contacting the shaped biological tissue with a cell lysis solution prior to cross-linking the biological tissue.

11. The method of claim 8, the cross-linking agent being selected from the group consisting of glutaraldehyde, formaldehyde, glyceraldehyde, paraformaldehyde, dialdehyde starch, and combinations thereof.

12. The method of claim 8, the alcohol being selected from the group consisting of ethanol, methanol, propanol, isopropanol, and combinations thereof and being present in the solution at a concentration of about 10% to about 90 by volume.

13. A method of preparing a fixed biological tissue, the method comprising:
   (a) harvesting at least one layer of biological tissue, the biological tissue being selected from the group consisting of pericardial tissue, peritoneal tissue, and pleural tissue, the layer of biological tissue comprising an inner lining of a serous membrane, and an outer lining of associated fascia, the layer of biological tissue comprising a plurality of cells;
   (b) contacting the layer of biological tissue with at least one solution that causes lysis of the cells;
   (c) at least partially cross-linking the biological tissue by contacting the biological tissue with a solution containing at least one cross-linking agent;
   (d) sterilizing the at least partially cross-linked biological tissue by contacting the biological tissue with a solution containing an alcohol; and
   (e) inactivating prions in the sterilized biological tissue, the prions in the biological tissue being inactivated by contacting the sterilized biological tissue with a basic solution having a molar concentration of about 0.5 M to about 4.0 M;
   whereby steps (a)-(e) are performed sequentially, wherein the layer of biological tissue is trimmed and shaped to a desired size and configuration.

14. The method of claim 13, further comprising applying at least one pharmacological agent to the fixed tissue, the at least one pharmacological agent being selected from the group consisting of an anti-inflammatory agent, an anti-proliferative agent, an anti-coagulation agent, or an anti-platelet aggregation agent.

* * * * *